(12) United States Patent
Ishii et al.

(10) Patent No.: US 7,034,184 B2
(45) Date of Patent: Apr. 25, 2006

(54) PROCESS FOR PRODUCING AZINE COMPOUNDS AND OXIME COMPOUNDS

(75) Inventors: Yasutaka Ishii, Takatsuki (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/379,604

(22) Filed: Mar. 6, 2003

(65) Prior Publication Data

US 2003/0204084 A1  Oct. 30, 2003

(30) Foreign Application Priority Data

Mar. 8, 2002  (JP) ............................. 2002-063232

(51) Int. Cl.
C07C 241/02 (2006.01)
C07C 241/04 (2006.01)
C07C 249/04 (2006.01)

(52) U.S. Cl. ...................... 564/249; 564/253; 546/245; 546/79

(58) Field of Classification Search ................ 546/245, 546/79; 564/249, 253
See application file for complete search history.

(56) References Cited

U.S. PATENT DOCUMENTS 6,355,842 B1   3/2002  Alsters et al.

FOREIGN PATENT DOCUMENTS

DE   0 758 642 A2   2/1997
DE      1004566 A2  10/1999
NL   WO 93/08160 A1  4/1993
US   0 690 045 A1   1/1996

OTHER PUBLICATIONS

European Search Report dated Jun. 24, 2003.

*Primary Examiner*—Rita Desai
(74) *Attorney, Agent, or Firm*—Birch, Stewart, Kolasch & Birch, LLP

(57) ABSTRACT

A process comprising allowing a peroxide compound represented by following Formula (2):

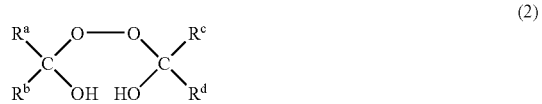

(2)

wherein $R^a$, $R^b$, $R^c$ and $R^d$ are the same or different and are each a hydrogen atom or a hydrocarbon group, and wherein $R^a$ and $R_b$, $R^c$ and $R^d$ may be combined to form a ring together with the adjacent carbon atom, respectively, to react with ammonia and water to yield an azine compound represented by following Formula (3):

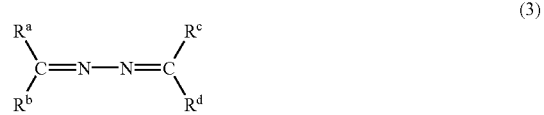

(3)

wherein $R^a$, $R^b$, $R^c$ and $R^d$ have the same meanings as defined above, or oxime compounds represented by following Formulae (4a) and/or (4b):

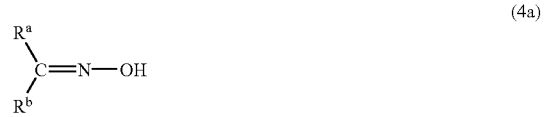

(4a)

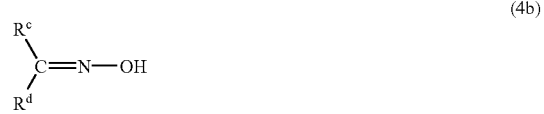

(4b)

wherein $R^a$, $R^b$, $R^c$ and $R^d$ have the same meanings as defined above, in the presence of a nitrogen-containing cyclic compound constitutively having a skeleton represented by following Formula (A) in its ring:

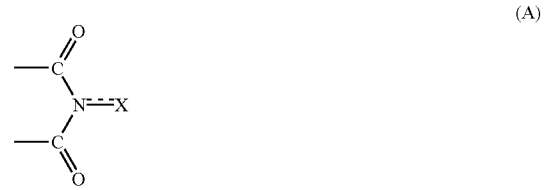

(A)

wherein X is one of an oxygen atom and an —OR group, and wherein R is one of a hydrogen atom and a hydroxyl-protecting group. This process can produce an oxime compound or an azine compound useful as a material for oxime compounds from low-cost materials by easy and simple procedures.

3 Claims, No Drawings

PROCESS FOR PRODUCING AZINE COMPOUNDS AND OXIME COMPOUNDS

This nonprovisional application claims priority under 35 U.S.C. § 119(a) on patent application Ser. No. 2002-063232 filed in JAPAN on Mar. 8, 2002, which is herein incorporated by reference.

BACKGROUND OF THE INVENTION

1. Field of the Invention

The present invention relates to a process for producing azine compounds and oxime compounds that are useful as intermediate materials for polyamides or as intermediates in the organic synthesis.

2. Description of the Related Art

Oxime compounds have been conventionally produced by, for example, a process of subjecting a carbonyl compound and hydroxylamine to dehydration condensation, a process of catalytically hydrogenating a nitroalkenone in the presence of a palladium catalyst, or a process of subjecting a hydroxyaminoalkane to air oxidation in the presence of a divalent cobalt. However, these processes require relatively expensive material compounds.

Cyclohexanone oxime is commercially produced by a process in which cyclohexane is irradiated with radiation in the presence of nitrosyl chloride to thereby yield cyclohexanone oxime via nitrosocyclohexane. This process can directly convert cyclohexane into cyclohexanone oxime and can thereby reduce production costs. However, nitrosyl chloride used as a raw material is generally prepared by a reaction between nitrogen monoxide and chlorine, thus invites complicated facilities and decreased operability and imposes heavy loads on the environment.

SUMMARY OF THE INVENTION

Accordingly, an object of the present invention is to provide a process for easily producing an oxime compound or an azine compound useful as a material for oxime compounds from low-cost materials.

Another object of the present invention is to provide a novel process for producing an oxime compound from an azine compound as a material.

After intensive investigations to achieve the objects, the present inventors have found a process using a nitrogen-containing cyclic compound having a specific structure can efficiently convert peroxide compounds into corresponding azine compounds and/or oxime compounds, or azine compounds into corresponding oxime compounds; can efficiently provide corresponding azine compounds and/or oxime compounds from at least one selected from compounds each having a methylene group, alcohol compounds and carbonyl compounds. The present invention has been accomplished based on these findings.

Specifically, the present invention provides, a process for producing an azine compound or an oxime compound (hereinafter may referred to as "process 1"), including allowing a peroxide compound represented by following Formula (2):

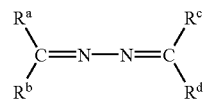

(2)

wherein $R^a$, $R^b$, $R^c$ and $R^d$ are the same or different and are each a hydrogen atom or a hydrocarbon group, and wherein $R^a$ and $R^b$, $R^c$ and $R^d$ may be combined to form a ring together with the adjacent carbon atom, respectively, to react with ammonia and water to yield an azine compound represented by following Formula (3):

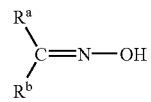

(3)

wherein $R^a$, $R^b$, $R^c$ and $R^d$ have the same meanings as defined above, or oxime compounds represented by following Formulae (4a) and/or (4b):

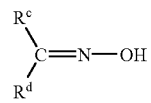

(4a)

(4b)

wherein $R^a$, $R^b$, $R^c$ and $R^d$ have the same meanings as defined above, in the presence of a nitrogen-containing cyclic compound constitutively having a skeleton represented by following Formula (A) in its ring:

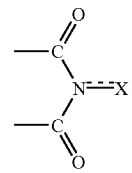

(A)

wherein X is one of an oxygen atom and an —OR group, and wherein R is one of a hydrogen atom and a hydroxyl-protecting group.

The present invention also provides, a process for producing an oxime compound (hereinafter may referred to as "process 2"), including allowing an azine compound represented by following Formula (3):

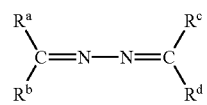

(3)

wherein $R^a$, $R^b$, $R^c$ and $R^d$ are the same or different and are each a hydrogen atom or a hydrocarbon group, and wherein $R^a$ and $R^b$, $R^c$ and $R^d$ may be combined to form a ring together with the adjacent carbon atom, respectively, to react with water to yield oxime compounds represented by following Formulae (4a) and/or (4b):

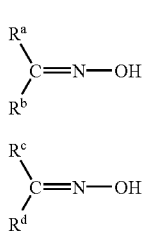

(4a)

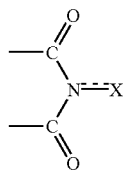

(4b)

wherein $R^a$, $R^b$, $R^c$ and $R^d$ have the same meanings as defined above, in the presence of a nitrogen-containing cyclic compound constitutively having a skeleton represented by following Formula (A) in its ring:

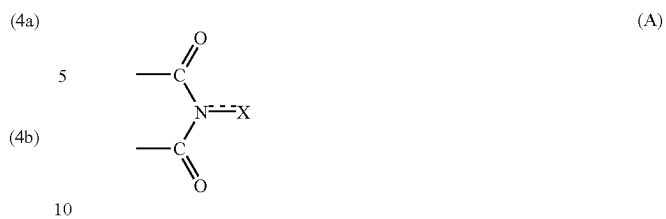

(A)

wherein X is one of an oxygen atom and an —OR group, and wherein R is one of a hydrogen atom and a hydroxyl-protecting group.

In another aspect, the present invention provides, a process for producing an azine compound or an oxime compound (hereinafter may referred to as "process 3"), including allowing at least one pair of compounds selected from three pairs of:

a pair of compounds each having a methylene group represented by following Formulae (5a) and (5b):

(5a)

(5b)

wherein $R^a$, $R^b$, $R^c$ and $R^d$ are the same or different and are each a hydrogen atom or a hydrocarbon group, and wherein $R^a$ and $R^b$, $R^c$ and $R^d$ may be combined to form a ring together with the adjacent carbon atom, respectively;

a pair of alcohol compounds represented by following Formulae (6a) and (6b):

(6a)

(6b)

wherein $R^a$, $R^b$, $R^c$ and $R^d$ have the same meanings as defined above; and a pair of carbonyl compounds represented by following Formulae (7a) and (7b):

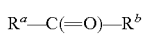

(7a)

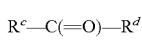

(7b)

wherein $R^a$, $R^b$, $R^c$ and $R^d$ have the same meanings as defined above, to react with oxygen, ammonia and water in the presence of a nitrogen-containing cyclic compound constitutively having a skeleton represented by following Formula (A) in its ring:

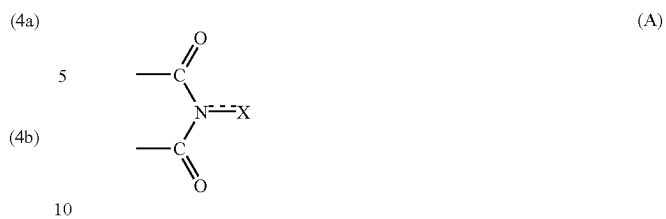

(A)

wherein X is one of an oxygen atom and an —OR group, and wherein R is one of a hydrogen atom and a hydroxyl-protecting group, to yield an azine compound represented by following Formula (3):

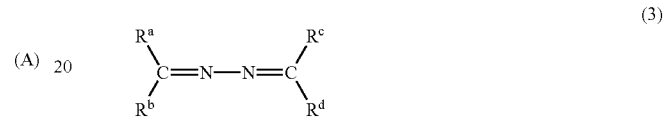

(3)

wherein $R^a$, $R^b$, $R^c$ and $R^d$ have the same meanings as defined above, or oxime compounds represented by following Formulae (4a) and/or (4b):

(4a)

(4b)

wherein $R^a$, $R^b$, $R^c$ and $R^d$ have the same meanings as defined above.

Examples of the nitrogen-containing cyclic compound include an imide compound having a cyclic imide skeleton represented by following Formula (I):

(I)

wherein n is one of 0 and 1; X is one of an oxygen atom and an —OR group, and wherein R is one of a hydrogen atom and a hydroxyl-protecting group.

According to the present invention, an oxime compound or an azine compound useful as a material for an oxime compound can be easily produced from low-cost materials. An oxime compound can be also efficiently produced from an azine compound.

In the present specification, "peroxide compound represented by Formula (2)" in process 1, "azine compound represented by Formula (3)" in process 2, and "at least one pair of compounds selected from three pairs of a pair of compounds each having a methylene group, a pair of alcohol compounds, and a pair of carbonyl compounds" in process 3 may simply referred to as "substrate".

Further objects, features and advantages of the present invention will become apparent from the following description of the preferred embodiments.

DESCRIPTION OF THE PREFERRED EMBODIMENT

Nitrogen-containing Cyclic Compounds

In the skeleton represented by Formula (A) constituting a nitrogen-containing cyclic compounds used in each process of the present invention, the bond between a nitrogen atom and X is a single or double bond. The nitrogen-containing cyclic compound may intramolecularly have a plurality of the skeleton represented by Formula (A). When X is an —OR group and R is a hydroxyl-protecting group, the nitrogen-containing cyclic compound may have a plurality of moieties combined through R, which moieties are derived from the skeleton represented by Formula (A) by removal of R.

In Examples of the hydroxyl-protecting group represented by R in Formula (A) are hydroxyl-protecting groups conventionally used in the field of organic synthesis. Such hydroxyl-protecting groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, 1-hydroxyalkyl groups (e.g., 1-hydroxyethyl, 1-hydroxyhexyl, 1-hydroxydecyl, 1-hydroxyhexadecyl, 1-hydroxy-1-phenylmethyl groups), and other groups capable of forming an acetal or hemiacetal group with a hydroxyl group; acyl groups (e.g., formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and other aliphatic $C_1$–$C_{20}$ acyl groups, and other aliphatic unsaturated or saturated acyl groups; acetoacetyl group; cyclopentanecarbonyl, cyclohexanecarbonyl, other cycloalkanecarbonyl groups, and other alicyclic acyl groups; benzoyl, naphthoyl, and other aromatic acyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., methoxycarbonyl, ethoxycarbonyl, t-butoxycarbonyl, and other $C_1$–$C_4$ alkoxy-carbonyl groups), aralkyloxycarbonyl groups (e.g., benzyloxycarbonyl, and p-methoxybenzyloxycarbonyl groups), substituted or unsubstituted carbamoyl groups (e.g., carbamoyl, methylcarbamoyl, and phenylcarbamoyl groups), groups derived from inorganic acids (e.g., sulfuric acid, nitric acid, phosphoric acid, and boric acid) by removal of OH group, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is an —OR group, a plurality of moieties may be combined through R, which moieties are derived from the skeleton of Formula (A) by removal of R. In this case, R includes, for example, oxalyl, malonyl, succinyl, glutaryl, adipoyl, phthaloyl, isophthaloyl, terephthaloyl, and other polycarboxylic acyl groups; carbonyl group; methylene, ethylidene, isopropylidene, cyclopentylidene, cyclohexylidene, benzylidene, and other polyvalent hydrocarbon groups, of which groups capable of forming an acetal bond with two hydroxyl groups are preferred.

Preferred examples of R are hydrogen atom; groups capable of forming an acetal or hemiacetal group (bond) with a hydroxyl group; acyl groups, sulfonyl groups, alkoxycarbonyl groups, carbamoyl groups, and other groups derived from acids (e.g., carboxylic acids, sulfonic acids, carbonic acid, carbamic acid, sulfuric acid, phosphoric acids, and boric acids) by removal of OH group, and other hydrolyzable protecting groups that can be eliminated by hydrolysis.

The nitrogen-containing cyclic compounds include, but are not limited to, cyclic imide compounds each having a N-substituted cyclic imide skeleton represented by Formula (I). These cyclic imide compounds may intramolecularly have a plurality of the N-substituted imide skeleton represented by Formula (I). When X is an —OR group and R is a hydroxyl-protecting group, the cyclic imide compounds may have a plurality of moieties (N-oxy cyclic imide skeletons) combined through R, which moieties are derived from the N-substituted cyclic imide skeleton represented by Formula (I) by removal of R.

In Formula (I), n is 0 or 1. Specifically, Formula (I) represents a five-membered N-substituted cyclic imide skeleton when n is 0 and represents a six-membered N-substituted cyclic imide skeleton when n is 1.

Typical examples of the imide compounds are imide compounds represented by following Formula (1):

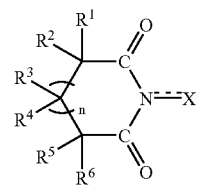

(1)

wherein n is one of 0 and 1;

X is one of an oxygen atom and an —OR group, wherein R is one of a hydrogen atom and a hydroxyl-protecting group;

$R^1$, $R^2$, $R^3$, $R^4$, $R^5$, and $R^6$ are the same or different and are each one of hydrogen atom, halogen atoms, alkyl groups, aryl group, cycloalkyl groups, hydroxyl group, alkoxy groups, carboxyl group, substituted oxycarbonyl groups, acyl groups, and acyloxy groups, wherein at least two of $R^1$, $R^2$, $R^3$, $R^4$, $R^5$, and $R^6$ may be combined to form a double bond, an aromatic ring, or a non-aromatic ring with a carbon atom or a carbon-carbon bond constituting the cyclic imide skeleton, and wherein one or more of an N-substituted cyclic imide group represented by following Formula (a):

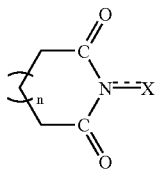

wherein n and X have the same meanings as defined above, may be further formed on at least one of $R^1$, $R^2$, $R^3$, $R^4$, $R^5$, and $R^6$ or at least one of the double bond, the aromatic ring and the non-aromatic ring formed by at least two of $R^1$, $R^2$, $R^3$, $R^4$, $R^5$, and $R^6$.

In the substituents $R^1$, $R^2$, $R^3$, $R^4$, $R^5$, and $R^6$ in the imide compounds, the halogen atoms include iodine, bromine, chlorine, and fluorine atoms. The alkyl groups include, for example, methyl, ethyl, propyl, isopropyl, butyl, isobutyl, s-butyl, t-butyl, hexyl, decyl, dodecyl, tetradecyl, hexadecyl, and other straight- or branched-chain alkyl groups each containing from about 1 to about 30 carbon atoms, of which those each containing from about 1 to about 20 carbon atoms are preferred.

The aryl groups include, for example, phenyl, tolyl, xylyl, and naphthyl groups. The cycloalkyl groups include, for example, cyclopentyl and cyclohexyl groups. The alkoxy groups include, for example, methoxy, ethoxy, isopropoxy, butoxy, t-butoxy, hexyloxy, octyloxy, decyloxy, dodecyloxy, tetradecyloxy, octadecyloxy, and other alkoxy groups each containing from about 1 to about 30 carbon atoms, of which alkoxy groups each containing from about 1 to about 20 carbon atoms are preferred.

The substituted oxycarbonyl groups include, but are not limited to, methoxycarbonyl, ethoxycarbonyl, isopropoxycarbonyl, butoxycarbonyl, t-butoxycarbonyl, hexyloxycarbonyl, decyloxycarbonyl, hexadecyloxycarbonyl, and other $C_1$–$C_{30}$ alkoxy-carbonyl groups, of which $C_1$–$C_{20}$ alkoxy-carbonyl groups are preferred; cyclopentyloxycarbonyl, cyclohexyloxycarbonyl, and other cycloalkyloxycarbonyl groups, of which cycloalkyloxycarbonyl groups each having 3 to 20 members are preferred; phenyloxycarbonyl, naphthyloxycarbonyl, and other aryloxycarbonyl groups, of which $C_6$–$C_{20}$ aryloxy-carbonyl groups are preferred; benzyloxycarbonyl, and other aralkyloxycarbonyl groups, of which $C_7$–$C_{21}$ aralkyloxy-carbonyl groups are preferred.

The acyl groups include, but are not limited to, formyl, acetyl, propionyl, butyryl, isobutyryl, valeryl, pivaloyl, hexanoyl, octanoyl, decanoyl, lauroyl, myristoyl, palmitoyl, stearoyl, other aliphatic $C_1$–$C_{30}$ acyl groups, and other unsaturated or saturated aliphatic acyl groups, of which aliphatic $C_1$–$C_{20}$ acyl groups are preferred; acetoacetyl group; cyclopentanecarbonyl, cyclohexanecarbonyl, other cycloalkanecarbonyl, and other alicyclic acyl groups; benzoyl, naphthoyl, and other aromatic acyl groups.

The acyloxy groups include, but are not limited to, formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, stearoyloxy, other aliphatic $C_1$–$C_{30}$ acyloxy groups, and other unsaturated or saturated aliphatic acyloxy groups, of which $C_1$–$C_{20}$ acyloxy groups are preferred; acetoacetyloxy group; cyclopentanecarbonyloxy, cyclohexanecarbonyloxy, other cycloalkanecarbonyloxy, and other alicyclic acyloxy groups; benzoyloxy, naphthoyloxy, and other aromatic acyloxy groups.

The substituents $R^1$, $R^2$, $R^3$, $R^4$, $R^5$, and $R^6$ may be the same with or different from one another. At least two of $R^1$, $R^2$, $R^3$, $R^4$, $R^5$, and $R^6$ in Formula (1) may be combined to form a double bond, an aromatic ring, or a non-aromatic ring with a carbon atom or carbon-carbon bond constituting the cyclic imide skeleton. The aromatic or non-aromatic ring contains preferably from about 5 to about 12 members and more preferably from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have at least one substituent, cyclohexene ring and other cycloalkene rings which may have at least one substituent), non-aromatic bridged rings (e.g., 5-norbornene ring and other bridged hydrocarbon rings which may have at least one substituent), benzene ring, naphthalene ring, and other aromatic rings (including condensed rings) which may have at least one substituent. The ring often comprises an aromatic ring. The ring may have at least one substituent. Such substituents include, but are not limited to, alkyl groups, haloalkyl groups, hydroxyl group, alkoxy groups, carboxyl group, substituted oxycarbonyl groups, acyl groups, acyloxy groups, nitro group, cyano group, amino group, and halogen atoms.

One or more of the N-substituted cyclic imide group represented by Formula (a) may be further formed on at least one of $R^1$, $R^2$, $R^3$, $R^4$, $R^5$, and $R^6$ and/or on the double bond, aromatic ring, or non-aromatic ring formed by the at least two of $R^1$, $R^2$, $R^3$, $R^4$, $R^5$, and $R^6$. For example, when at least one of $R^1$, $R^2$, $R^3$, $R^4$, $R^5$, and $R^6$ is an alkyl group containing two or more carbon atoms, the N-substituted cyclic imide group may be formed with adjacent two carbon atoms constituting the alkyl group. Likewise, when at least two of $R^1$, $R^2$, $R^3$, $R^4$, $R^5$, and $R^6$ are combined to form a double bond with a carbon-carbon bond constituting the cyclic imide skeleton, the N-substituted cyclic imide group may be formed with the double bond. When at least two of $R^1$, $R^2$, $R^3$, $R^4$, $R^5$, and $R^6$ are combined to form an aromatic or non-aromatic ring with a carbon atom or carbon-carbon bond constituting the cyclic imide skeleton, the N-substituted cyclic imide group may be formed with adjacent two carbon atoms constituting the ring.

Preferred imide compounds include compounds represented by following formulae:

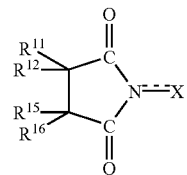

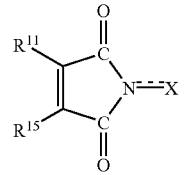

-continued

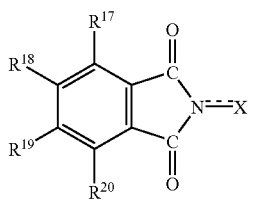
(1c)

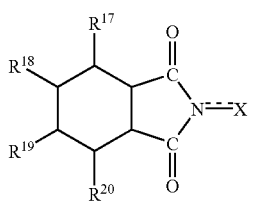
(1d)

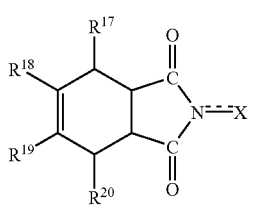
(1e)

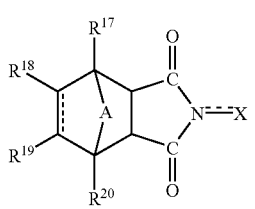
(1f)

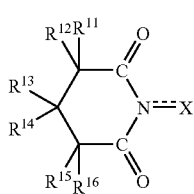
(1g)

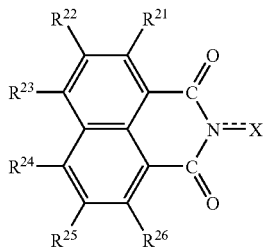
(1h)

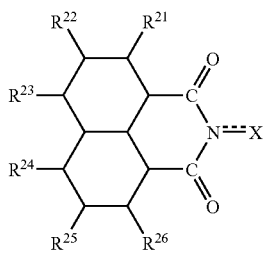
(1i)

wherein $R^{11}$, $R^{12}$, $R^{13}$, $R^{14}$, $R^{15}$, and $R^{16}$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups;

$R^{17}$, $R^{18}$, $R^{19}$, $R^{20}$, $R^{21}$, $R^{22}$, $R^{23}$, $R^{24}$, $R^{25}$, and $R^{26}$ are the same or different and are each one of hydrogen atom, alkyl groups, haloalkyl groups, hydroxyl group, alkoxy groups, carboxyl group, substituted oxycarbonyl groups, acyl groups, acyloxy groups, nitro group, cyano group, amino group, and halogen atoms, wherein adjacent two of $R^{17}$ to $R^{26}$ may be combined to form a five- or six-membered N-substituted cyclic imide skeleton indicated in one of Formulae (1c), (1d), (1e), (1f), (1h), and (1i);

A in Formula (1f) is a methylene group or an oxygen atom; and

X has the same meaning as defined above.

The halogen atoms, alkyl groups, aryl groups, cycloalkyl groups, hydroxyl group, alkoxy groups, carboxyl group, substituted oxycarbonyl groups, acyl groups, and acyloxy groups in the substituents $R^{11}$ to $R^{16}$ include the same groups as in the corresponding groups in the substituents $R^1$ to $R^6$.

In the substituents $R^{17}$ to $R^{26}$, the alkyl groups include the same alkyl groups as those exemplified above, of which alkyl groups each containing from about 1 to about 6 carbon atoms are preferred. The haloalkyl groups include, for example, trifluoromethyl group, and other haloalkyl groups each containing from about 1 to about 4 carbon atoms. The alkoxy groups include the same alkoxy groups as those exemplified above, of which lower alkoxy groups each containing from about 1 to about 4 carbon atoms are preferred. The substituted oxycarbonyl groups include the same substituted oxycarbonyl groups as those exemplified above, such as alkoxycarbonyl groups, cycloalkyloxycarbonyl groups, aryloxycarbonyl groups, and aralkyloxycarbonyl groups. The acyl groups include aliphatic unsaturated or saturated acyl groups, acetoacetyl group, alicyclic acyl groups, aromatic acyl groups, and other acyl groups as exemplified above. The acyloxy groups include aliphatic unsaturated or saturated acyloxy groups, acetoacetyloxy group, alicyclic acyloxy groups, aromatic acyloxy groups, and other acyloxy groups as exemplified above. The halogen atoms include, for example, fluorine, chlorine, and bromine atoms. Each of the substituents $R^{17}$ to $R^{26}$ is often one of hydrogen atom, lower alkyl groups each containing from about 1 to about 4 carbon atoms, carboxyl group, substituted oxycarbonyl groups, nitro group, and halogen atoms.

Examples of preferred imide compounds having a five-membered N-substituted cyclic imide skeleton are N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-chloro-N-hydroxyphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N- hydroxyphthalimide, N-hydroxy-4,5-bis(pentyloxycarbonyl)phthalimide, 4,5-bis(dodecyloxycarbonyl)-N-hydroxyphthalimide, N-hydroxy-4,5-bis(phenoxycarbonyl)phthalimide, and other compounds of Formula (1) wherein X is an —OR group and R is a hydrogen atom; compounds corresponding to these compounds, except with R of an acyl group such as acetyl group, propionyl group, and benzoyl group; N-methoxymethyloxyphthalimide, N-(2-methoxyethoxymethyloxy)phthalimide, N-tetrahydropyranyloxyphthalimide, and other compounds of Formula (1) wherein X is an —OR group and R is a group capable of forming an acetal or hemiacetal bond with a hydroxyl group; N-methanesulfonyloxyphthalimide, N-(p-toluenesulfonyloxy)phthalimide, and other compounds of Formula (1) wherein X is an —OR group and R is a sulfonyl group; sulfuric esters, nitric esters, phosphoric esters, and boric esters of N-hydroxyphthalimide, and other compounds of Formula (1) wherein X is an —OR group and R is a group derived from an inorganic acid by removal of OH group.

Examples of preferred imide compounds each having a six-membered N-substituted cyclic imide skeleton are N-hydroxyglutarimide, N-hydroxy-α,α-dimethylglutarimide, N-hydroxy-β,β-dimethylglutarimide, N-hydroxy-1,8-decalindicarboximide, N,N'-dihydroxy-1,8;4,5-decalintetracarboxylic diimide, N-hydroxy-1,8-naphthalenedicarboximide (N-hyrdoxynaphthalimide), N,N'-dihydroxy-1,8;4,5-naphthalenetetracarboxylic diimide, and other compounds of Formula (1) wherein X is an —OR group and R is a hydrogen atom; compounds corresponding to these compounds except with R of an acyl group such as acetyl group, propionyl group, and benzoyl group; N-methoxymethyloxy-1,8-naphthalenedicarboximide, N,N'-bis(methoxymethyloxy)-1,8;4,5-naphthalenetetracarboxylic diimide, and other compounds of Formula (1) wherein X is an —OR group and R is a group capable of forming an acetal or hemiacetal bond with a hydroxyl group; N-methanesulfonyloxy-1,8-naphthalenedicarboximide, N,N'-bis(methanesulfonyloxy)-1,8;4,5-naphthalenetetracarboxylic diimide, and other compounds of Formula (1) wherein X is an —OR group and R is a sulfonyl group; sulfuric esters, nitric esters, phosphoric esters, and boric esters of N-hydroxy-1,8-naphthalenedicarboximide and N,N'-dihydroxy-1,8;4,5-naphthalenetetracarboxylic diimide, and other compounds of Formula (1) wherein X is an —OR group and R is a group derived from an inorganic acid by removal of OH group.

In addition to the cyclic imide compounds, the nitrogen-containing cyclic compounds include, for example, cyclic acylurea compounds each having a cyclic acylurea skeleton [—C(=O)—N—C(=O)—N—] represented by following Formula (II):

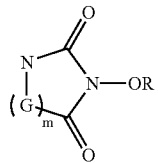
(II)

wherein G is one of a carbon atom and a nitrogen atom; m is one of 1 and 2, and, when m is 2, two Gs may be the same or different; and R has the same meaning as defined above. These cyclic acylurea compounds may each intramolecularly have a plurality of the cyclic acylurea skeleton represented by Formula (II). They also may have a plurality of moieties (N-oxy cyclic acylurea skeletons) combined through R, which moieties are derived from the cyclic acylurea skeleton of Formula (II) by removal of R. The atom G and the nitrogen atom combined with G constituting the cyclic acylurea skeleton may have at least one substituent. The cyclic acylurea skeleton may further have a non-aromatic or aromatic ring condensed therewith and/or may have a double bond in its ring.

The cyclic acylurea skeletons represented by Formula (II) include a 3-hydroxy (or 3-substituted oxy) hydantoin skeleton represented by following Formula (IIa); a 4-hydroxy (or 4-substituted oxy)-1,2,4-triazolidine-3,5-dione skeleton [inclusive of a 4-hydroxy (or 4-substituted oxy)-1,2,4-triazoline-3,5-dione skeleton]] represented by following Formula (IIb); a hydro-3-hydroxy (or 3-substituted oxy)-1,3-diazine-2,4-dione skeleton [inclusive of a hexahydro-1-hydroxy (or 1-substituted oxy)-1,3-diazine-2,4,6-trione skeleton, a hexahydro-1,3-dihydroxy (or 1,3-bis-substituted oxy)-1,3-diazine-2,4,6-trione skeleton, and a 3-hydroxy (or 3-substituted oxy) uracil skeleton] represented by following Formula (IIc); a hydro-4-hydroxy (or 4-substituted oxy)-1,2,4-triazine-3,5-dione skeleton represented by following Formula (IId); a hydro-1-hydroxy (or 1-substituted oxy)-1,3,5-triazine-2,6-dione skeleton represented by following Formula (IIe); and a hydro-5-hydroxy (or 5-substituted oxy)-1,2,3,5-tetrazine-4,6-dione skeleton represented by following Formula (IIf):

(IIa)

(IIb)

(IIc)

(IId)

(IIe)

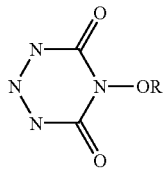

(IIf)

wherein R has the same meaning as defined above.

Typical examples of the cyclic acylurea compounds are hydro-1-hydroxy (or 1-substituted oxy)-1,3,5-triazine-2,6-dione compounds represented by following Formula (14):

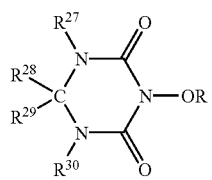

(14)

wherein $R^{27}$ and $R^{30}$ are the same or different and are each one of hydrogen atom, alkyl groups, aryl groups, cycloalkyl groups, hydroxyl groups which may be protected by a protecting group, carboxyl groups which may be protected by a protecting group, and acyl groups;

$R^{28}$ and $R^{29}$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups, wherein at least two of $R^{27}$, $R^{28}$, $R^{29}$, and $R^{30}$ may be combined to form one of a double bond, an aromatic ring, or a non-aromatic ring with an atom constituting the ring in the formula, wherein $R^{28}$ and $R^{29}$ may together form an oxo group; and R has the same meaning as defined above.

In Formula (14), the alkyl groups, aryl groups, cycloalkyl groups, and acyl groups in $R^{27}$ and $R^{30}$ are similar to those exemplified in the substituents $R^1$ to $R^6$. The hydroxyl-protecting group herein includes similar hydroxyl-protecting groups as exemplified above.

Examples of the carboxyl-protecting group include protecting groups conventionally used in the field of organic synthesis. Such carboxyl-protecting groups include, but are not limited to, methoxy, ethoxy, butoxy, and other $C_1$–$C_6$ alkoxy groups, and other alkoxy groups; cycloalkyloxy groups; phenoxy group, and other aryloxy groups; benzyloxy, and other aralkyloxy groups; trimethylsilyloxy group, and other trialkylsilyloxy groups; amino group, methylamino group, dimethylamino group, and other mono- or di-$C_1$–$C_6$ alkyl-amino groups, and other amino groups which may have at least one substituent.

Examples of the halogen atoms, alkyl groups, aryl groups, cycloalkyl groups, hydroxyl group, alkoxy groups, carboxyl group, substituted oxycarbonyl groups, acyl groups, and acyloxy groups in $R^{28}$ and $R^{29}$ are similar to those exemplified in the substituents $R^1$ to $R^6$.

At least two of $R^{27}$, $R^{28}$, $R^{29}$, and $R^{30}$ may be combined to form one of a double bond, an aromatic ring, and a non-aromatic ring with at least one atom (a carbon atom and/or a nitrogen atom) constituting the ring in Formula (2), and $R^{28}$ and $R^{29}$ may together form an oxo group. Preferred examples of the aromatic ring and the non-aromatic ring are similar to those exemplified above.

Preferred examples of the cyclic acylurea compounds are 3-hydroxyhydantoin, 1,3-dihydroxyhydantoin, and their derivatives, and other compounds each having the skeleton represented by Formula (IIa); 4-hydroxy-1,2,4-triazolidine-3,5-dione, 4-hydroxy-1,2,4-triazoline-3,5-dione, and their derivatives, and other compounds having the skeleton represented by Formula (IIb); hexahydro-3-hydroxy-1,3-diazine-2,4-dione, hexahydro-1,3-dihydroxy-1,3-diazine-2,4-dione, hexahydro-1-hydroxy-1,3-diazine-2,4,6-trione, hexahydro-1,3-dihydroxy-1,3-diazine-2,4,6-trione, 3-hydroxyuracil, and their derivatives, and other compounds having the skeleton represented by Formula (IIc); hexahydro-4-hydroxy-1,2,4-triazine-3,5-dione, and their derivatives, and other compounds having the skeleton represented by Formula (IId); hexahydro-1,3,5-trihydroxy-1,3,5-triazine-2,4,6-trione, 1,3,5-triacetoxy-hexahydro-1,3,5-triazine-2,4,6-trione, 1,3,5-tris(benzoyloxy)-hexahydro-1,3,5-triazine-2,4,6-trione, hexahydro-1,3,5-tris(methoxymethyloxy)-1,3,5-triazine-2,4,6-trione, hexahydro-1-hydroxy-1,3,5-triazine-2,6-dione, hexahydro-1-hydroxy-3,5-dimethyl-1,3,5-triazine-2,6-dione, 1-acetoxy-hexahydro-1,3,5-triazine-2,6-dione, 1-acetoxy-hexahydro-3,5-dimethyl-1,3,5-triazine-2,6-dione, 1-benzoyloxy-hexahydro-1,3,5-triazine-2,6-dione, 1-benzoyloxy-hexahydro-3,5-dimethyl-1,3,5-triazine-2,6-dione, and other compounds having the skeleton represented by Formula (IIe) such as compounds represented by Formula (14); hexahydro-5-hydroxy-1,2,3,5-tetrazine-4,6-dione, and their derivatives, and other compounds having the skeleton represented by Formula (IIf).

Among the nitrogen-containing cyclic compounds, compounds wherein X is an —OR group and R is a hydrogen atom (N-hydroxy cyclic compounds) can be prepared according to a known procedure or a combination of such procedures. Compounds wherein X is an —OR group and R is a hydroxyl-protecting group can be prepared by introducing a desired protecting group into a corresponding compound wherein R is a hydrogen atom (N-hydroxy cyclic compounds) according to a conventional reaction procedure for the introduction of protecting groups.

More specifically, among the cyclic imide compounds, compounds wherein X is an —OR group and R is a hydrogen atom (N-hydroxy cyclic imide compounds) can be prepared by a conventional imidization process such as a process that comprises the steps of allowing a corresponding acid anhydride to react with hydroxylamine for ring-opening of an acid anhydride group, and closing the ring to form an imide. For example, N-acetoxyphthalimide can be prepared by allowing N-hydroxyphthalimide to react with acetic anhydride or to react with an acetyl halide in the presence of a base. These compounds can also be prepared by other processes.

Typically preferred imide compounds are N-hydroxysuccinimide, N-hydroxyphthalimide, N,N'-dihydroxypyromellitic diimide, N-hydroxyglutarimide, N-hydroxy-1,8-naphthalenedicarboximide, N,N'-dihydroxy-1,8;4,5-naphthalenetetracarboxylic diimide, and other N-hydroxyimide compounds derived from aliphatic polycarboxylic anhydrides (cyclic anhydrides) or aromatic polycarboxylic anhydrides (cyclic anhydrides); and compounds derived from the N-hydroxyimide compounds by introduction of a protecting group into a hydroxyl group thereof.

Among the cyclic acylurea compounds, for example, 1,3,5-triacetoxy-hexahydro-1,3,5-triazine-2,4,6-trione (i.e., 1,3,5-triacetoxyisocyanuric acid) can be prepared by allowing hexahydro-1,3,5-trihydroxy-1,3,5-triazine-2,4,6-trione (i.e., 1,3,5-trihydroxyisocyanuric acid) to react with acetic anhydride or to react with an acetyl halide in the presence of a base.

Each of the nitrogen-containing cyclic compounds having the skeleton represented by Formula (A) as a constituent of their ring can be used alone or in combination in the reaction. For example, a cyclic imide compound having the cyclic imide skeleton of Formula (I) can be used in combination with a cyclic acylurea compound having the cyclic acylurea skeleton of Formula (II). The nitrogen-containing cyclic compound(s) can be formed in the reaction system.

Promoter (Co-catalyst)

In each process of the present invention, where necessary, a promoter (co-catalyst) can be used in combination with the nitrogen-containing cyclic compound (catalyst). Such promoters include, but are not limited to, vanadium compounds, manganese compounds, cobalt compounds, compounds of Group 1 and Group 2 metal elements of the Periodic Table of Elements; and organic onium salts. In addition, promoters for imide compound catalysts described in, for example, Japanese Unexamined Patent Application Publication No. 09-327626 can also be used. Each of these promoters can be used alone or in combination. The reaction system may further comprise an initial activator such as a radical initiator (azobisisobutyronitrile), a radical reaction accelerator, and an oxidizing agent.

The amount of the radical initiator is, for example, from about 0.0000001 to about 0.5mole, preferably from about 0.0001 to about 0.3 mole per mole of the substrate. The reaction system may also comprise a stabilizer such as ethylenediaminetetraacetic acid (EDTA) as a trapping agent for intermediates such as peroxides for stabilizing the intermediates. The amount of the trapping agent is, for example, from about 0.0000001 to about 0.1 mole, preferably from about 0.00001 to about 0.01 mole per mole of the substrate.

Process 1

The process 1 of the present invention comprises allowing a peroxide compound represented by Formula (2) to react with ammonia and water to yield an azine compound represented by Formula (3) or oxime compounds represented by Formulae (4a) and/or (4b) in the presence of the nitrogen-containing cyclic compound.

In Formula (2), the hydrocarbon groups of $R^a$, $R^b$, $R^c$ and $R^d$ include aliphatic hydrocarbon groups, alicyclic hydrocarbon groups, aromatic hydrocarbon groups, and groups each comprising a plurality of these groups. Such aliphatic hydrocarbon groups include, but are not limited to, methyl, ethyl, propyl, isopropyl, butyl, isobutyl, t-butyl, pentyl, isopentyl, hexyl, octyl, decyl, dodecyl, tetradecyl, and other alkyl groups (e.g., $C_1$–$C_{20}$ alkyl groups); vinyl, allyl, and other alkenyl groups (e.g., $C_2$–$C_{20}$ alkenyl groups); ethynyl, propinyl, and other alkynyl groups (e.g., $C_2$–$C_{20}$ alkynyl groups). The alicyclic hydrocarbon groups include, but are not limited to, cyclopropyl, cyclobutyl, cyclopentyl, cyclohexyl, cyclooctyl, cyclodecyl, cyclododecyl, and other cycloalkyl groups (e.g., 3- to 20-membered cycloalkyl groups); cyclopentenyl, cyclohexenyl, and other cycloalkenyl groups (e.g., 3- to 20-membered cycloalkenyl groups). Another ring (an aromatic or non-aromatic carbon ring or heterocyclic ring) may be condensed to the alicyclic ring of the alicyclic hydrocarbon groups. In this case, abridged ring may be formed. The aromatic hydrocarbon groups include, for example, phenyl, naphthyl, and other aromatic hydrocarbon groups each having from about 6 to about 20 carbon atoms.

Among them, $C_1$–$C_{20}$ alkyl groups, 3- to 20-membered cycloalkyl groups, $C_6$–$C_{20}$ aromatic hydrocarbon groups, and groups each comprising a plurality of these groups combined with each other are preferred.

These hydrocarbon groups may have various substituents within a range not adversely affecting the reaction. Such substituents include, but are not limited to, halogen atoms, hydroxyl group, mercapto group, substituted oxy groups (e.g., alkoxy groups, aryloxy groups, and acyloxy groups), substituted thio groups, carboxyl group, substituted oxycarbonyl groups (e.g., alkoxycarbonyl groups), substituted or unsubstituted carbamoyl groups, cyano group, nitro group, substituted or unsubstituted amino groups, heterocyclic groups, and oxo groups.

$R^a$ and $R^b$, $R^c$ and $R^d$ may be combined to form a ring together with the adjacent carbon atom. The ring include, for example, cyclopropane ring, cyclobutane ring, cyclopentane ring, cyclohexane ring, cycloheptane ring, cyclooctane ring, cyclononane ring, cyclodecane ring, cyclododecane ring, cyclotetradecane ring, cyclohexadecane ring, cyclooctadecane ring, cycloicosane ring, cyclodocosanev, cyclotriacontane ring, and other 3- to 40-membered cycloalkane rings, of which 3- to 30-membered cycloalkane rings are preferred; cyclopentene ring, cyclohexene ring, and other 3- to 40-membered cycloalkene rings, of which 3- to 30-membered cycloalkene rings are preferred. Among them, cyclopentane ring, cyclohexane ring, cyclooctane ring, cyclododecane ring, and other about 5- to 20-membered cycloalkane rings are preferred.

The cycloalkane ring may have various substituents within a range not adversely affecting the reaction. The substituents include, in addition to the substituents that the hydrocarbon groups may have, for example, alkyl groups (e.g., methyl, ethyl, isopropyl, t-butyl, hexyl, octyl, decyl, and other $C_1$–$C_{20}$ alkyl groups, specifically, $C_1$–$C_4$ alkyl groups), alkenyl groups, alkynyl groups, cycloalkyl groups, cycloalkenyl groups, aryl groups (e.g., phenyl, and naphthyl groups), aralkyl groups (e.g., benzyl groups). An aromatic or non-aromatic carbon ring or heterocyclic ring may be condensed to the cycloalkane rings. In this case, a bridged ring may be formed.

Typical examples of the peroxide compounds having a ring formed by combining $R^a$ and $R^b$, and $R^c$ and $R^d$ together with the adjacent carbon atom, respectively, are bis(1-hydroxycycloalkyl) peroxides represented by following Formula (8):

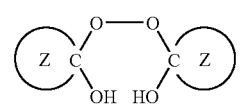

(8)

wherein ring Z is a cycloalkane ring.

The cycloalkane rings of the ring Z are the cycloalkane rings as defined above. The cycloalkane ring may have at least one substituent as defined above. An aromatic or non-aromatic carbon ring or heterocyclic ring may be condensed to the cycloalkane rings. In this case, a bridged ring may be formed.

Chain compounds of the peroxide compounds represented by Formula (2) include, but are not limited to, bis(1-hydroxy-1-phenylmethyl) peroxide, bis(1-hydroxy-1-methylethyl) peroxide, bis(1-hydroxy-1-methylpropyl) peroxide, bis(1-hydroxy-1-phenylethyl) peroxide, and bis(1-hydroxy- 1,1-diphenyl) peroxide. Typical examples of the bis(1-hydroxycycloalkyl) peroxides represented by Formula (8) are bis(1-hydroxycyclopropyl) peroxide, bis(1-hydroxycyclobutyl) peroxide, bis(1-hydroxycyclopentyl) peroxide, bis(1-hydroxycyclohexyl) peroxide, bis(1-hydroxycycloheptyl) peroxide, bis(1-hydroxycyclooctyl) peroxide, bis(1-hydroxycyclononyl) peroxide, bis(1-hydroxycyclodecyl) peroxide, bis(1-hydroxycyclotetradecyl) peroxide, bis(1-hydroxycyclohexadecyl) peroxide, and bis(1-hydroxycyclooctadecyl) peroxide.

The peroxide compound represented by Formula (2) can be prepared by, for example, allowing the alcohol compound represented by Formula (6a) and the carbonyl compound represented by Formula (7b) [or, the alcohol compound represented by Formula (6b) and the carbonyl compound represented by Formula (7a)] to react with molecular oxygen in the presence of the imide compound having the cyclic imide skeleton represented by Formula (I) [refer to PCT International Publication No. WO99/50204 (PCT/JP99/01464)]. The reaction is performed in the presence of, or in the absence of, a solvent. Such solvents include, but are not limited to, acetic acid, propionic acid, and other organic acids; acetonitrile, benzonitrile, and other nitrites; formamide, acetamide, dimethylformamide (DMF), dimethylacetamide, and other amides; hexane, octane, and other aliphatic hydrocarbons; dichloromethane, chloroform, 1,2-dichloroethane, dichlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. The amount of the carbonyl compound is, for example, from about 0.5 to about 5 mole per mole of the alcohol compound. The amount of the imide compound is, for example, from about 0.000001 to about 1 mole per mole of the alcohol compound. The molecular oxygen is not specifically limited and includes pure oxygen, oxygen diluted with an inert gas, and air. A reaction temperature is from about 30° C. to about 150° C. The reaction can be performed at atmospheric pressure or under a pressure (under a load). Where necessary, manganese compound, cobalt compound, and other metallic compounds can be used as a promoter (co-catalyst). When a compound corresponding the alcohol compound represented by Formula (6a) is used as the carbonyl compound represented by Formula (7b), a symmetrical peroxide compound can be formed.

The peroxide compound represented by Formula (2) can also be prepared by allowing the compound having a methylene group represented by Formula (5a) and the compound having a methylene group represented by Formula (5b) to react with molecular oxygen in the presence of the imide compound having the cyclic imide skeleton represented by Formula (I). The compound having a methylene group represented by Formula (5a) and the compound having a methylene group represented by Formula (5b) may be the same compound. In this case, a symmetrical peroxide compound can be formed. The reaction is performed in the presence of, or in the absence of, a solvent. Such solvents may be the same solvents as defined above. The amount of the imide compound is, for example, from about 0.000001 to about 1 mole per mole of the compound having a methylene group. The molecular oxygen is not specifically limited and includes pure oxygen, oxygen diluted with an inert gas, and air. A reaction temperature is from about 60° C. to about 150° C. The reaction can be performed at atmospheric pressure or under a pressure (under a load).

Where necessary, manganese compound, cobalt compound, and other metallic compounds can be used as a promoter (co-catalyst).

Furthermore, the peroxide compound represented by Formula (2) can be prepared by allowing the carbonyl compound represented by Formula (7a) and the carbonyl compound represented by Formula (7b) to react with hydrogen peroxide. The carbonyl compound represented by Formula (7a) and the carbonyl compound represented by Formula (7b) may be the same compound. In this case, a symmetrical peroxide compound can be formed.

In the process 1 of the present invention, ammonia may be ammonia gas using as intact or in the form of a solution prepared by dissolving the ammonia gas in an appropriate organic solvent or water. The ammonia gas may be diluted with an inert gas such as nitrogen, helium, argon or carbon. The amount of ammonia is generally more than 0.5 mole, for example, from about 0.5 to about 100 mole, preferably from about 1 to about 50 mole per mole of the substrate. The water may be used in excess to the substrate. The amount of the nitrogen-containing cyclic compound can be selected within a broad range and is, for example, from about 0.0000001 to about 2 mole, preferably 0.0001 to 1 mole, more preferably 0.01 to 0.8 mole, and often from about to 0.05 to about 0.8 mole per mole of the substrate. Where necessary, the stabilizer as defined above can be added to the system. Hydroxylamine can also be added.

The reaction is performed in the presence of, or in the absence of, a solvent. Such solvents are similar to those exemplified in the process for preparation of peroxide compound represented by Formula (2).

A reaction temperature can appropriately selected depending on the type of the substrate within a range of, for example, from about 0° C. to about 200° C., preferably from about 10° C. to about 100° C. The reaction can be performed at atmospheric pressure or under a pressure (under a load). The reaction can be performed in a batch system, semi-batch system, continuous system or another conventional system.

According to the reaction of the present process, azine compounds represented by Formula (3) corresponding peroxide compounds represented by Formula (2) used as a material, and/or oxime compounds represented by Formula (4a), and/or oxime compounds represented by Formula (4b) can be formed. Specifically, when the bis(1-hydroxycycloalkyl) peroxides represented by Formula (8) are used as a material, cycloalkanone azines represented by following Formula (9):

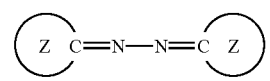

(9)

wherein ring Z has the same meanings as defined above, and/or cycloalkanone oximes represented by following Formula (10):

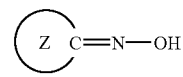

(10)

wherein ring Z has the same meanings as defined above, can be formed.

Chain compounds of the azine compounds represented by Formula (3) include, for example, benzaldehyde, azine, acetone azine, methylethylketone azine, acetophenone azine, and benzophenone azine. Typical examples of cycloalkanone azines represented by Formula (9) are cyclopropanone azine, cyclobutanone azine, cyclopentanone azine, cyclohexanone azine, cycloheptanone azine, cyclooctanone azine, cyclononanone azine, cyclodecanone azine, cyclododecanone azine, cyclotetradecanone azine, cyclohexadecanone azine, and cyclooctadecanone azine.

Chain compounds of the oxime compounds represented by Formulae (4a) and (4b) include, but are not limited to, benzaldehyde oxime, acetone oxime, methylethylketone oxime, acetophenone oxime, and benzophenone oxime. Typical examples of cycloalkanone oximes represented by Formula (10) are cyclopropanone oxime, cyclobutanone oxime, cyclopentanone oxime, cyclohexanone oxime, cycloheptanone oxime, cyclooctanone oxime, cyclononanone oxime, cyclodecanone oxime, cyclododecanone oxime, cyclotetradecanone oxime, cyclohexadecanone oxime, and cyclooctadecanone oxime.

In the process 1, the production ratio of azine compound and oxime compound is controlled by appropriately selecting reaction conditions such as the reaction temperature, reaction time, the type and amount of the substrate, the type of the solvent, the amount of water. By lengthening a total reaction time or by increasing amount of the nitrogen-containing cyclic compound used for the reaction, the production ratio of oxime compound is increased. After the completion of the reaction, reaction products can be separated and purified by a technique such as filtration, concentration, distillation, extraction, crystallization, recrystallization, adsorption, column chromatography, and other separation means, or any combination of these separation means.

Process 2

The process 2 of the present invention comprises allowing an azine compound represented by Formula (3) to react with water to yield oxime compounds represented by Formulae (4a) and/or (4b) in the presence of the nitrogen-containing cyclic compound constitutively having the skeleton represented by Formula (A) in its ring.

The substituents $R^a$, $R^b$, $R^c$ and $R^d$ in Formula (3) have the same meanings as defined above. Preferred $R^a$, $R^b$, $R^c$ and $R^d$ include $C_1$–$C_{20}$ alkyl groups, 3- to 20-membered cycloalkyl groups, $C_6$–$C_{20}$ aromatic hydrocarbon groups, and groups each comprising a plurality of these groups combined with each other. Compounds represented by Formula (3), wherein $R^a$ and $R^b$, $R^c$ and $R^d$ may be combined to form a ring together with the adjacent carbon atom, are also preferred. Examples of the azine compounds include the cycloalkanone azines represented by Formula (9). Among them, cyclopentanone azine, cyclohexanone azine, cyclooctanone azine, cyclododecanone azine, and other 5- to 20-membered cycloalkanone azines are preferred. The azine compounds represented by Formula (3) can be prepared by the process 1 of the present invention.

The amount of water in process 2 is generally more than 0.5 mole, for example, from about 0.5 to about 100 mole, and preferably from about 1 to about 50 mole per mole of the substrate. The water may often be used in excess to the substrate. The amount of the nitrogen-containing cyclic compound can be selected within a broad range and is, for example, from about 0.0000001 to about 5 mole, preferably 0.0001 to 3 mole, more preferably 0.01 to 2 mole, and often from about to 0.1 to about 1.5 mole per mole of the substrate.

Where necessary, ammonia, hydroxylamine, or the stabilizer as defined above can be added to the system for improving the reaction rate and yields.

The reaction is performed in the presence of, or in the absence of, a solvent. Such solvents may be the same solvents as defined above. A reaction temperature can appropriately selected depending on the type of the substrate from the range of, for example, from about 0° C. to about 200° C., and preferably from about 10° C. to about 100° C. The reaction can be performed at atmospheric pressure or under a pressure (under a load). The reaction can be performed in a batch system, semi-batch system, continuous system or another conventional system.

According to the reaction of the present process, an oxime compound represented by Formula (4a), and/or an oxime compound represented by Formula (4b) corresponding an azine compound represented by Formula (3) used as a material can be formed. Specifically, when cycloalkanone azines represented by Formula (9) are used as a material in the reaction, cycloalkanone oximes represented by Formula (10) can be formed.

After the completion of the reaction, reaction products can be separated and purified by a technique such as filtration, concentration, distillation, extraction, crystallization, recrystallization, adsorption, column chromatography, and other separation means, or any combination of these separation means.

Process 3

The process 3 of the present invention comprises allowing at least one pair of compounds selected from three pairs of: a pair of compounds each having a methylene group represented by Formulae (5a) and (5b): a pair of alcohol compounds represented by Formulae (6a) and (6b): and a pair of carbonyl compounds represented by Formulae (7a) and (7b): to react with oxygen, ammonia and water in the presence of a nitrogen-containing cyclic compound constitutively having a skeleton represented by Formula (A) in its ring to yield an azine compound represented by Formula (3) or oxime compounds represented by Formulae (4a) and/or (4b).

The compound represented by Formula (5a) and the compound represented by Formula (5b), the compound represented by Formula (6a) and the compound represented by Formula (6b), and the compound represented by Formula (7a) and the compound represented by Formula (7b) may be the same compound, respectively. In this case, a symmetrical azine compound and/or a single oxime compound can be formed.

In the process 3, (i) a compound having a methylene group (e.g., cycloalkanes), or (ii) a mixture of an alcohol compound (e.g., cycloalkanols) and a carbonyl compound (e.g., cycloalkanones) such as K/A oil is often used as a substrate.

$R^a$, $R^b$, $R^c$ and $R^d$ in Formulae (5a), (5b), (6a), (6b), (7a) and (7b) have the same meanings as defined above. Preferred substituents $R^a$, $R^b$, $R^c$ and $R^d$ include $C_1$–$C_{20}$ alkyl groups, 3- to 20-membered cycloalkyl groups, $C_6$–$C_{20}$ aromatic hydrocarbon groups, and groups each comprising a plurality of these groups combined with each other are preferred. Compounds of the Formulae (5a), (5b), (6a), (6b), (7a), and (7b), wherein $R^a$ and $R^b$, $R^c$ and $R^d$ may be combined to form a ring together with the adjacent carbon atom, are also preferred. Typical examples of compounds each having a methylene group, alcohol compounds, and carbonyl compounds, wherein $R^a$ and $R^b$, $R^c$ and $R^d$ may be combined to form a ring together with the adjacent carbon atom, are cycloalkanes, cycloalkanols, and cycloalkanones represented by following Formulae (11), (12), and (13), respectively:

 (11)

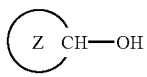 (12)

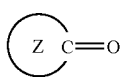 (13)

wherein ring Z has the same meanings as defined above.

Chain compounds of the compounds each having a methylene group represented by Formulae (5a) and (5b) include, but are not limited to, toluene, propane, butane, ethylbenzene, and phenylmethylbenzene. Typical examples of cycloalkanes represented by Formula (11) are, for example, cyclopropane, cyclobutane, cyclopentane, cyclohexane, cycloheptane, cyclooctane, cyclononane, cyclodecane, cyclododecane, cyclotetradecane, cyclohexadecane, cyclooctadecane, cycloicosane, cyclodocosane, cyclotriacontane, and other 3- to 40-membered cycloalkane. Among them, cyclopentane, cyclohexane, cyclooctane, cyclododecane, and other 5- to 20-membered cycloalkanes are preferred.

Chain compounds of the alcohol compounds represented by Formulae (6a) and (6b) include, but are not limited to, benzyl alcohol, isopropyl alcohol, s-butyl alcohol, α-methylbenzyl alcohol, and benzhydrol. Typical examples of cycloalkanols represented by Formula (12) are, for example, cycloalkanols corresponding the cycloalkanes as defined above such as cyclopropanol, cyclobutanol, cyclopentanol, cyclohexanol, cycloheptanol, cyclooctanol, cyclononanol, cyclodecanol, cyclododecanol, cyclotetradecanol, cyclohexadecanol, cyclooctadecanol, cycloicosanol, cyclodocosanol, cyclotriacontanol, and other 3- to 40-membered cycloalkanols, of which about 3- to 30-membered cycloalkanols are prefered. Among them, cyclopentanol, cyclohexanol, cyclooctanol, cyclododecanol, and other 5- to 20-membered cycloalkaneols are preferred.

Chain compounds of the carbonyl compounds represented by Formulae (7a) and (7b) include, but are not limited to, benzaldehyde, acetone, mehylethylketone, acetophenone, and bezophenone. Typical examples of cycloalkanones represented by Formula (13) are, for example, cycloalkanone corresponding the cycloalkane as defined above such as cyclopropanone, cyclobutanone, cyclopentanone, cyclohexanone, cycloheptanone, cyclooctanone, cyclononanone, cyclodecanone, cyclododecanone, cyclotetradecanone, cyclohexadecanone, cyclooctadecanone, cycloicosanone, cyclodocosanone, cyclotriacontanone, and other 3- to 40-membered cycloalkanones, of which 3- to 30-membered cycloalkanones are preferred. Among them, cyclopentanone, cyclohexanone, cyclooctanone, cyclododecanone, and other 5- to 20-membered cycloalkanones are preferred.

The oxygen may be any of molecular oxygen and active oxygen. The molecular oxygen is not specifically limited and includes pure oxygen, oxygen diluted with an inert gas such as nitrogen, helium, argon or carbon dioxide, and air. The amount of oxygen depends on the type of the substrate, and is generally more than 0.5 mole (e.g., more than 1 mole), preferably from about 1 to about 100 mole, and more preferably from 2 to 50 mole per mole of the substrate. The oxygen may often be used in excess to the substrate.

Ammonia may be ammonia gas using as intact or in the form of a solution prepared by dissolving the ammonia gas in an appropriate organic solvent or water. The ammonia gas may be diluted with an inert gas such as nitrogen, helium, argon or carbon. The amount of ammonia is generally more than 0.5 mole, for example, from about 0.5 to about 100 mole, preferably from about 1 to about 50 mole per mole of the substrate.

The amount of water used in the reaction is generally more than 0.5 mole, for example, from about 0.5 to about 100 mole, and preferably from about 1 to 50 mole per mole of the substrate. The water may be used in excess to the substrate. The amount of the nitrogen-containing cyclic compound can be selected within a broad range and is, for example, from about 0.0000001 to about 5 mole, preferably 0.0001 to 3 mole, and more preferably 0.01 to 2 mole per mole of the substrate.

The reaction is performed in the presence of, or in the absence of, a solvent. Such solvents may be the same solvents as defined above. A reaction temperature can appropriately selected depending on the type of the substrate from the range of, for example, from about 0° C. to about 200° C., preferably from about 10° C. to about 100° C. The reaction can be performed at atmospheric pressure or under a pressure (under a load). The reaction can be performed in a batch system, semi-batch system, continuous system or another conventional system in the presence of ammonia and oxygen or under through ammonia and oxygen.

The reaction may progress with some steps. For example, a mixture of the substrate, the nitrogen-containing cyclic compound, and where necessary, radical initiator and solvent is allowed to react in the presence of oxygen, and subsequently water, ammonia, and where necessary, stabilizer are added to the system to react for a specific time, and thereby an azine compound and/or an oxime compound are formed. The mechanism is probably as follows. For example, in the former step, peroxide compounds represented by Formula (2) are initially formed, and peroxide compounds represented by Formula (2) undergoes conversion to thereby yield the target compound in the latter step. Water may be added at the former step.

According to the reaction of the present invention, the azine compound represented by Formula (3) and/or the oxime compounds represented by Formulae (4a) and/or (4b), which corresponds to the compounds each having a methylene group represented by Formulae (5a) and (5b), the alcohol compounds represented by Formulae (6a) and (6b), or the carbonyl compounds represented by Formulae (7a) and (7b) used as a material, can be formed. The production ratio of the azine compound and the oxime compound is controlled by appropriately selecting reaction conditions such as the reaction temperature, reaction time, the type and the amount of the substrate, the type of the solvent, the amount of water.

After the completion of the reaction, reaction products can be separated and purified by a technique such as filtration, concentration, distillation, extraction, crystallization, recrystallization, adsorption, column chromatography, and other separation means, or any combination of these separation means.

The formed azine compounds and oxime compounds in each process of the present invention can be used as materials for medicine, agricultural chemicals, dye, solvent, explosive and polyamide (nylon). Specifically, 6- to 12-membered cycloclkanone azines and cycloalkanone oximes are useful as materials for polyamide.

EXAMPLES

The present invention will be illustrated in further detail with reference to several examples below, which are not intended to limit the scope of the invention. Reaction mixtures were analyzed by gas chromatography or high-performance liquid chromatography.

Example 1

1 mmole of bis(1-hydroxycyclohexyl) peroxide [corresponding to the compound of Formula (8) wherein the ring Z is a cyclohexane ring], 0.6 mmole of N-hydroxyphthalimide, 3 ml of acetonitrile and 4 ml of water were placed in a flask and were stirred at 55° C. in an atmosphere of ammonia gas (1 atm=0.101 MPa) for 12 hours. The resulting reaction mixture was extracted with diisopropyl ether and the organic layer was analyzed to find to yield 0.35 mmole of cyclohexanone azine [corresponding to the compound of Formula (9) wherein the ring Z is a cyclohexane ring] and 0.52 mmole of cyclohexanone oxime [corresponding to the compound of Formula (10) wherein the ring Z is a cyclohexane ring].

Example 2

1 mmole of bis(1-hydroxycyclohexyl) peroxide, 0.6 mmole of N-hydroxyphthalimide, 5 mg of EDTA.2Na (disodium ethylenediaminetetraacetate), 3 ml of acetonitrile and 4 ml of water were placed in a flask and were stirred at 55° C. in an atmosphere of ammonia gas (1 atm=0.101 MPa) for 12 hours. The resulting reaction mixture was extracted with diisopropyl ether and the organic layer was analyzed to find to yield 0.31 mmole of cyclohexanone azine and 0.52 mmole of cyclohexanone oxime.

Comparative Example 1

The procedure of Example 1 was repeated, except that N-hydroxyphthalimide was not used, and thereby yielded 0.04 mmole of cyclohexanone azine and 0.03 mmole of cyclohexanone oxime.

Comparative Example 2

The procedure of Example 1 was repeated, except that water was not used, and thereby yielded 0.02 mmole of cyclohexanone azine. Cyclohexanone oxime wasn't yielded at all.

Example 3

3 mmole of cyclohexanone, 6 mmole of cyclohexanol, 0.6 mmole of N-hydroxyphthalimide, 0.3 mmole of AIBN (azobisisobutyronitrile) and 3 ml of acetonitrile were placed in a flask and were stirred at 55° C. in an atmosphere of oxygen gas (1 atm=0.101 MPa) for 19 hours. Subsequently, 5 mg of EDTA.2Na and 4 ml of water were added to the mixture and were stirred at 30° C. in an atmosphere of ammonia gas (1 atm=0.101 MPa) for 0.5 hours. The resulting reaction mixture was extracted with diisopropyl ether and the organic layer was analyzed to find to yield 0.87 mmole of cyclohexanone azine and 0.43 mmole of cyclohexanone oxime.

Example 4

1 mmole of cyclohexanone azine, 0.6 mmole of N-hydroxyphthalimide, 5 mg of EDTA.2Na, 3 ml of acetonitrile and 4 ml of water were placed in a flask and were stirred at 55° C. in an atmosphere of ammonia gas (1 atm=0.101 MPa) for 12 hours. The resulting reaction mixture was extracted with diisopropyl ether and the organic layer was analyzed to find to yield 0.56 mmole of cyclohexanone oxime. 0.67 mmole of unreacted cyclohexanone azine was remained.

Example 5

The procedure of Example 4 was repeated, except that 1.2 mmole of N-hydroxyphthalimide was used, and thereby yielded 0.99 mmole of cyclohexanone oxime. 0.31 mmole of unreacted cyclohexanone azine was remained.

Example 6

The procedure of Example 4 was repeated, except that acetonitrile was not used, and thereby yielded 0.41 mmole of cyclohexanone oxime. 0.71 mmole of unreacted cyclohexanone azine was remained.

Example 7

The procedure of Example 4 was repeated, except that the reaction was performed in an atmosphere of argon gas instead of ammonia gas, and thereby yielded 0.48 mmole of cyclohexanone oxime. 0.41 mmole of unreacted cyclohexanone azine was remained.

Comparative Example 3

The procedure of Example 4 was repeated, except that water was not used. Cyclohexanone oxime was not yielded at all and unreacted cyclohexanone azine was collected.

Comparative Example 4

The procedure of Example 4 was repeated, except that N-hydroxyphthalimide was not used. Cyclohexanone oxime was not yielded at all and 0.83 mmole of unreacted cyclohexanone azine was recovered.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing an azine compound or an oxime compound, the process comprising reacting a peroxide compound represented by following Formula (2)

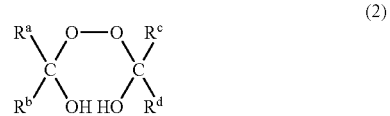

wherein $R^a$, $R^b$, $R^c$ and $R^d$ are the same or different and are each a hydrogen atom or a hydrocarbon group, and wherein $R^a$ and $R^b$, $R^c$ and $R^d$ may be combined to form a ring together with the adjacent carbon atom, respectively, with ammonia and water in the presence of a nitrogen-containing cyclic compound constitutively having a skeleton represented by following Formula (A) in its ring:

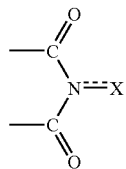
(A)

wherein X is one of an oxygen atom and an —OR group, and wherein R is one of a hydrogen atom and a hydroxyl-protecting group, to yield an azine compound represented by following Formula (3):

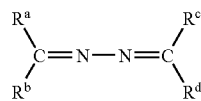
(3)

wherein $R^a$, $R^b$, $R^c$ and $R^d$ have the same meanings as defined above, or oxime compounds represented by following Formulae (4a) and/or (4b):

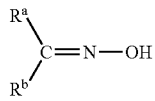
(4a)

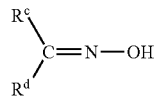
(4b)

wherein $R^a$, $R^b$, $R^c$ and $R^d$ have the same meanings as defined above.

2. The process according to claim 1, wherein the nitrogen-containing cyclic compound is an imide compound having a cyclic imide skeleton represented by following Formula (I):

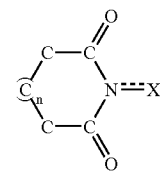
(I)

wherein n is one of 0 and 1; X is one of an oxygen atom and an —OR group, and wherein R is one of a hydrogen atom and a hydroxyl-protecting group.

3. The process according to claim 1, wherein $R^a$, $R^b$, $R^c$ and $R^d$ are the same or different and are at least one selected from the group consisting of a hydrogen atom, a $C_1$–$C_{20}$ alkyl group, a 3- to 20-membered cycloalkyl group, a $C_6$–$C_{20}$ aromatic hydrocarbon group, and a group comprising a plurality of these groups combined with each other, or wherein $R^a$ and $R^b$ may be combined to form a ring, and $R^c$ and $R^d$ may be combined to form a ring, comprising a 5- to 20-membered cycloalkane ring together with the adjacent carbon atom, respectively.

* * * * *